(12) United States Patent
Parker

(10) Patent No.: US 7,293,363 B1
(45) Date of Patent: Nov. 13, 2007

(54) DUAL LINE PROTRACTOR FOR BIOMETRIC MEASUREMENTS

(76) Inventor: Emmett L. Parker, 1808 Gadsden Hwy. Ste. 136, Birmingham, AL (US) 35235

( * ) Notice: Subject to any disclaimer, the term of this patent is extended or adjusted under 35 U.S.C. 154(b) by 0 days.

(21) Appl. No.: 11/244,309

(22) Filed: Oct. 5, 2005

(51) Int. Cl.
*B43L 7/10* (2006.01)
(52) U.S. Cl. .............................. 33/471; 33/512; 33/1 N
(58) Field of Classification Search .................. 33/471, 33/512, 414, 424, 534, 415, 1 LE, 1 R, 1 N
See application file for complete search history.

(56) References Cited

U.S. PATENT DOCUMENTS

| | | | | | |
|---|---|---|---|---|---|
| 532,001 | A | * | 1/1895 | Linden | 33/471 |
| 1,399,963 | A | * | 12/1921 | Hogg | 33/280 |
| 1,590,499 | A | | 6/1926 | Cozad | |
| 2,586,074 | A | | 2/1952 | Memluck | |
| 2,872,733 | A | * | 2/1959 | Chew | 33/1 LE |
| 3,066,416 | A | * | 12/1962 | Gutting | 33/1 F |
| 3,126,637 | A | | 3/1964 | Short | |
| D204,805 | S | | 5/1966 | Gartman et al. | |
| 3,959,885 | A | * | 6/1976 | Edmiston | 33/1 R |
| 4,192,078 | A | * | 3/1980 | Lore et al. | 33/414 |
| 4,731,933 | A | | 3/1988 | Cope | |
| 4,771,548 | A | | 9/1988 | Donnery | |
| 5,163,228 | A | * | 11/1992 | Edwards et al. | 33/1 N |
| D337,955 | S | | 8/1993 | Edwards | |
| 5,263,492 | A | * | 11/1993 | Voyce | 33/471 |
| 5,732,474 | A | * | 3/1998 | Cannon | 33/452 |
| 5,792,077 | A | | 8/1998 | Gomes | |
| 6,209,213 | B1 | * | 4/2001 | Moe | 33/471 |
| 6,345,448 | B1 | | 2/2002 | Chontos | |
| 6,505,412 | B2 | * | 1/2003 | Hauzie, Jr. | 33/529 |
| 2001/0037581 | A1 | * | 11/2001 | Akhavan-Sigari et al. | 33/807 |
| 2006/0142671 | A1 | * | 6/2006 | Solak | 600/595 |

* cited by examiner

*Primary Examiner*—G. Bradley Bennett
*Assistant Examiner*—Travis Reis
(74) *Attorney, Agent, or Firm*—Gerald M. Walsh; Kenneth M. Bush; Bush Intellectual Property Law

(57) ABSTRACT

A dual line protractor fixed to a central axis which has two housings, each housing having a spool with retractable lines, the housings and spools being rotatably attached to the central axis. The spools and housings rotate independently of each other on the central axis. The lines can be extended from the spools and the tips of the lines are attached to anatomical landmarks on first and second body members. The protractor is placed on a joint between the first and second body members. The lines extend from the spools and housings over degree marks on the protractor. The difference between the degree marks provide the angle between the body members at the joint. The application of the dual line protractor for these measurements is simple and rapid, requiring only a few minutes, so that the range of motion of several joints with several repeat measurements can be performed in a relatively short period of time. Placing the tips of the lines on anatomical landmarks produces remarkable accuracy and precision in the measurement of joint angles. Because string-like lines are used to indicate the degree marks, the dual line protractor does not interfere with the natural motion of the body member being measured, allowing accurate dynamic joint angle measurement.

14 Claims, 4 Drawing Sheets

DUAL LINE PROTRACTOR FOR BIOMETRIC MEASUREMENTS

BACKGROUND OF THE INVENTION

1. Field of the Invention

The present invention relates to goniometers for measuring angles between body members and, more particularly, to a dual line protractor to measure the angle between two body members at a joint between the members at any desired orientation between the members.

2. Technical Background

The range of motion of a body joint is commonly measured to determine the presence and extent of joint abnormalities or the degree of healing and recovery from joint injuries. After a joint related injury a patient is often directed to limit the range of motion of a joint. Success of physical therapy and recovery is typically evaluated by improved ranges of motion of the injured joint. Goniometers are known which are adapted for measuring the range of motion of flexing joints such as knees, ankles, wrists, shoulders, hips, fingers, and the like. Early goniometers consisted of protractors with one fixed arm and one moveable arm. These devices were cumbersome, unreliable, and difficult to mount. They could interfere with the motion of the limb they were intended to measure and were not particularly useful. More recent devices using electronic means of measuring angular relationships suffer from similar problems. Some devices use a beam of energy, such as infrared light from a light emitting diode, reflectors, and detectors such as transistors. These electronic devices are complex, expensive, and can suffer from lack of accuracy and precision due to variations in the direction of the energy beam or consistent detection of an energy beam.

Protractors with chalk lines are known to mark lines at a given angle. These devices are accurate and precise over relatively long distances. They are easy to use, simple in construction, and inexpensive. Another advantage of these devices is that they use string lines which conform to irregularities of a surface without affecting precision or accuracy in setting an angle. However, they have not been adaptable as goniometers to measure angles of body members. What is needed is a line protractor that will measure body limb or member angles with the same ease and accuracy as obtained with protractor chalk lines that set angles.

SUMMARY OF THE INVENTION

The present invention is a dual line protractor in which the protractor is fixed to a central axis. Two housings are rotatably connected to the central axis. In each housing is a spool that is also rotatably connected to the central axis. The spools are wound with retractable lines, with the spools being biased to retract the lines. The lines extend through a hollow guide attached to each housing. As the lines extend from the housing they pass over a degree mark on the protractor. Each housing with its spool rotates independently of the other housing and its spool. The tip of a first line can be attached to an anatomical landmark on a first body member, the tip of a second line can be attached to an anatomical landmark on a second body member, and the protractor can be placed over the joint between the two body members. The protractor can be rotated so that the first line extends over any desired first degree mark. As the second body member is positioned as desired relative to the first body member, the second line will extend over a second degree mark on the protractor. The difference between the first degree mark and the second degree mark provides the angle between the two members at the joint between them.

An advantage of the present invention is a simple dual line protractor that measures body joint angles with excellent precision and accuracy.

Another advantage is a dual line protractor that measures body joint angles quickly and easily.

Another advantage is a dual line protractor that can measure the extent of joint rotation of most body joints.

Another advantage is a dual line protractor that can measure any joint angle as the relative positions of two body members sharing the same joint move with respect to each other.

Another advantage is the ability to measure dynamic joint angles in addition to static joint angles.

Another advantage is that the tip of the line can be attached directly to a specific anatomical landmark on a body member, producing remarkable accuracy and precision in the measurement of angles between the anatomical landmarks and between the body members.

Another advantage is a dual line protractor that is sturdy and inexpensive to manufacture.

DETAILED DESCRIPTION OF THE INVENTION

While the following description details the preferred embodiments of the present invention, it is to be understood that invention is not limited in its application to the details of construction and arrangement of the parts illustrated in the accompanying drawings, since the invention is capable of other embodiments and of being practiced in various ways.

Figure 1:
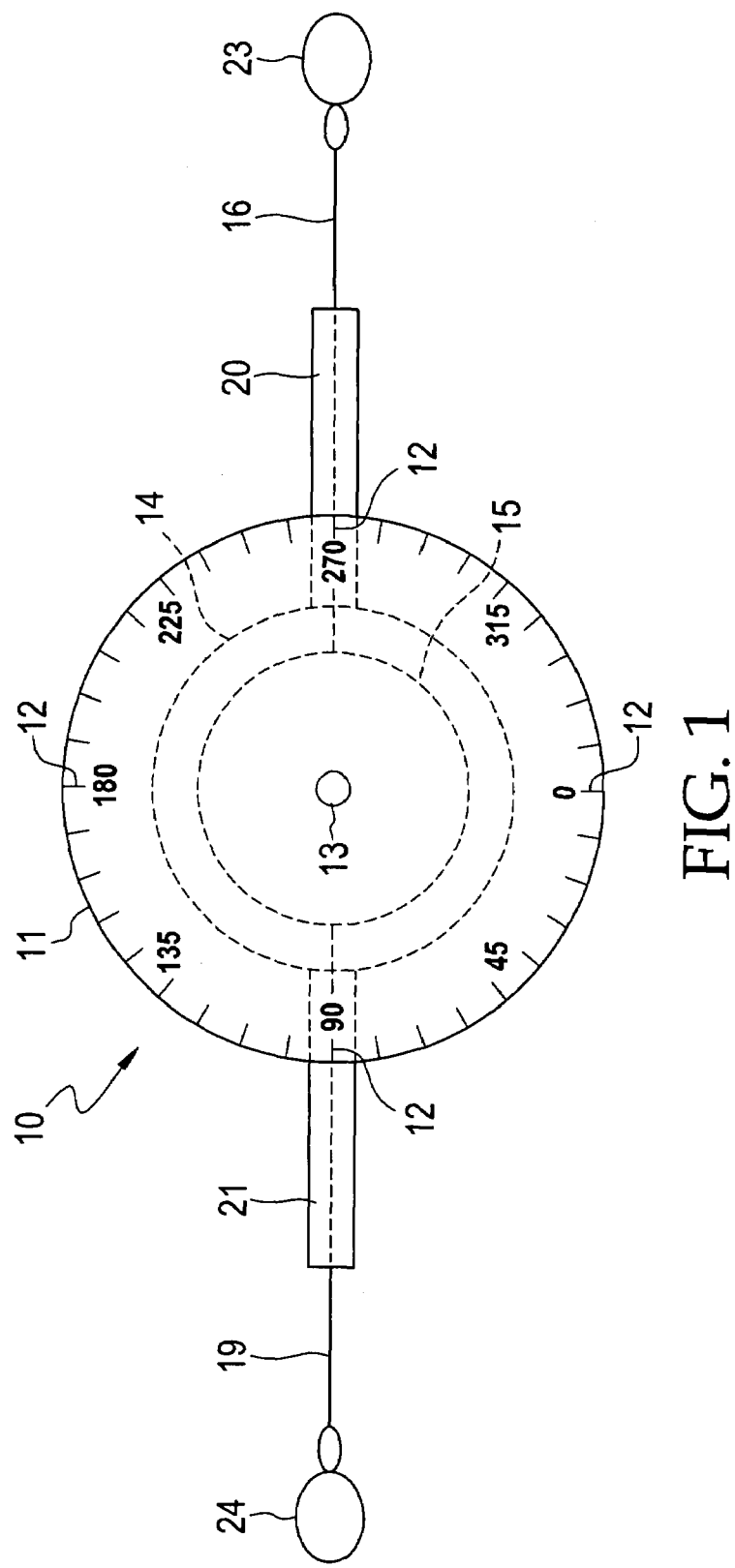
FIG. 1 shows a front view of the dual line protractor of the present invention.

FIG. 1 shows a front view of the dual line protractor 10 of the present invention. The protractor 11 has degree marks 12 typical of protractors known in the art. The protractor 11 is, preferably, a 360 degree protractor. Protractor 11 is fixed to a central axis 13. Behind protractor 11 is a first circular housing 14 which is attached rotatably to the central axis 13. A first spool 15 is inside first housing 14 and first spool 15 is also attached rotatably to the central axis 13. A first line 16 is wound around first spool 15. First spool 15 is biased to retract or rewind first line 16 onto first spool 15, by mechanisms well known in the art, such as, for example, by a spring mechanism (not shown) connected to first spool 15 and central axis 13. A second circular housing 17 with a second spool 18 having a second line 19 is behind first circular housing 14, which can be seen in FIG. 2a. First housing 14 has a hollow guide 20 through which first line 16 can extend and second housing 17 has a hollow guide 21 through which second line 19 can extend. As lines 16 and 19 extend through guides 20 and 21 they pass over a degree mark 12 on protractor 11. The protractor 11 can be rotated to position any desired degree mark at one of the lines. The difference in degrees between the degree marks over which the lines 16 and 19 are positioned provides the angle formed by lines 16 and 19.

Figure 2A:
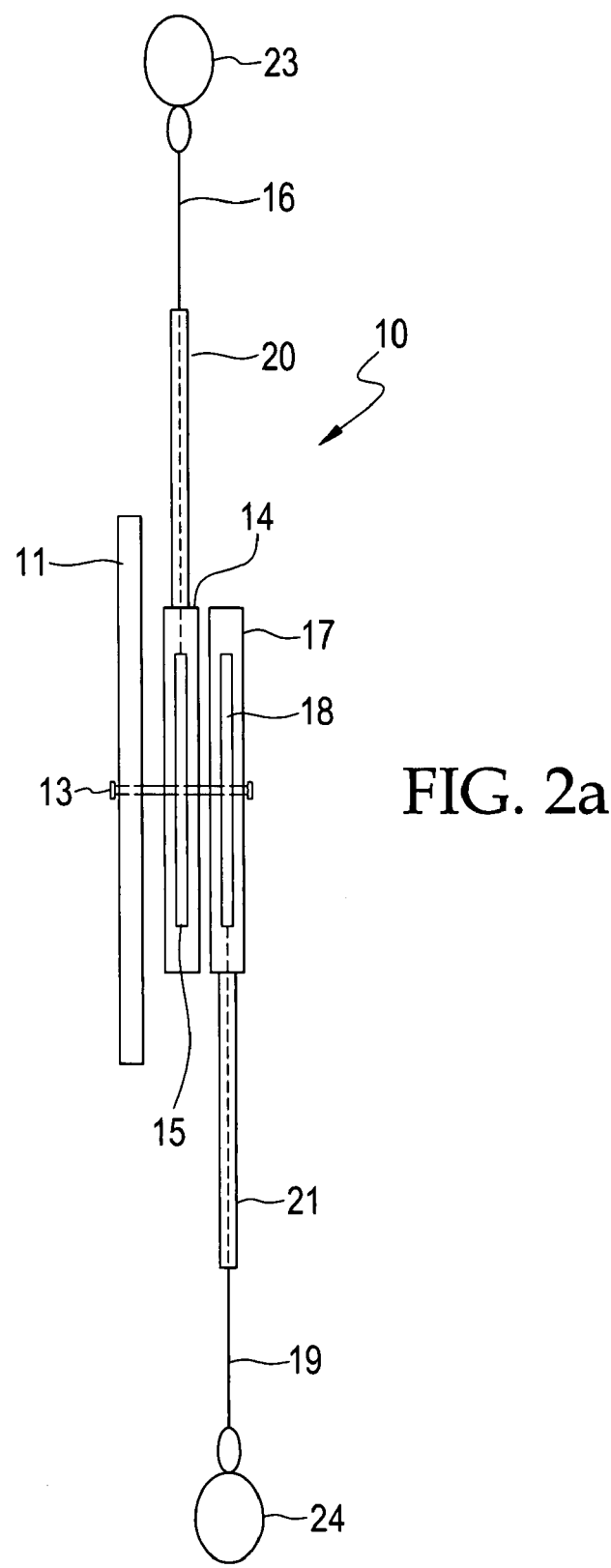
FIGS. 2a and 2b show side views of the dual line protractor.

FIG. 2a shows a side view of the dual line protractor 10. The position of second housing 17 relative to first housing 14 can be seen in this figure. Second circular housing 17 is also attached rotatably to the central axis 13. A second spool 18 is inside second housing 17 and second spool 18 is also attached rotatably to the central axis 13. A second line 19 is wound around second spool 18. Second spool 18 is also biased to retract or rewind second line 19 onto second spool 18, similar to first spool 15. First housing 14, first spool 15, second housing 17, second spool 18 rotate independently of each other on central axis 13. The tip of first line 16 has an attachment means 23 and the tip of second line 19 has an attachment means 24. The attachment means 23 and 24 prevent lines 16 and 19 from being completely retracted onto spools 15 and 18, and allow attachment of lines 16 and 19 to body members.

Figure 2B:
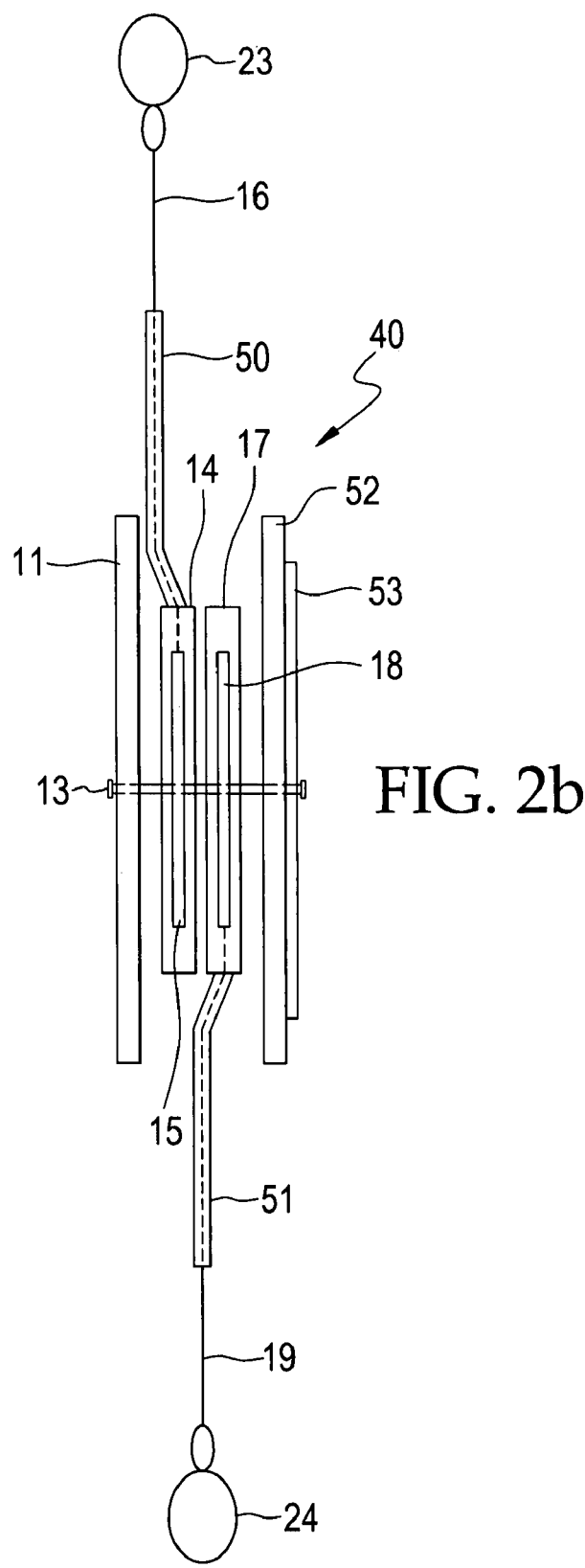

FIG. 2b shows an alternate embodiment of the present invention. The hollow guides 50 and 51 can be angled towards protractor 11 so that lines 16 and 19 are brought closer to the degree marks on protractor 11. The dual line protractor 40 of this embodiment can have a base 52 opposite protractor 11 with housings 14 and 17 positioned in between protractor 11 and base 52. Base 52 is fixed to axis 13, similar to protractor 11. Base 52 can have an attachment means 53, such as, for example, a hook and pile arrangement, to provide more secure attachment of dual line protractor 40 to a body area or joint. The hook or pile element 53 can have an adhesive to hold the element securely to the body area or joint. Base 52 is particularly useful when a more secure attachment is needed for certain measurements, such as, for example, dynamic joint angle measurements. Using dual line protractor 40, the movements of the lines 16 and 19 across degree marks 12 as a patient moves a body member can be recorded with photographic and/or video devices known in the art. The rate and extent of joint angle movement can be calculated from these recordings by methods known in the art.

The various elements of the present invention can be constructed of any suitable materials, but the protractor 11, housings 14 and 17, and the spools 15 and 18 are, preferably, made of clear plastic so that lines 16 and 19 can be easily visualized. The dual line protractor can be made in any suitable size and thickness.

Figure 3A:
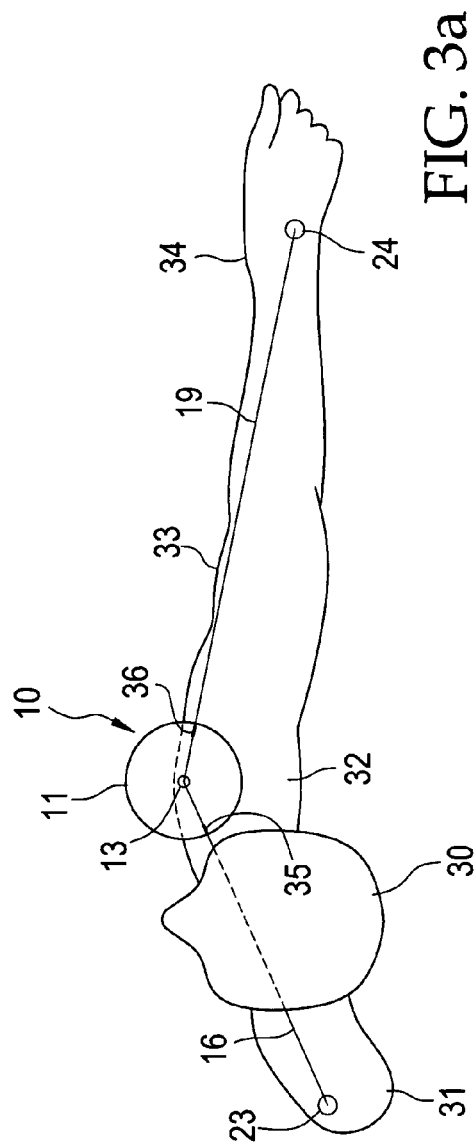
FIGS. 3a and 3b illustrate the use of the dual line protractor to measure angles between body members at a joint between the body members.
Figure 3B:
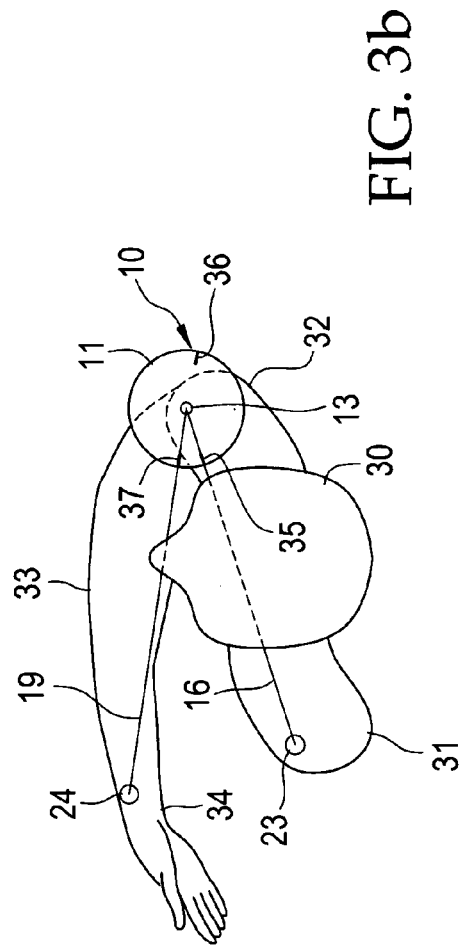

FIGS. 3a and 3b illustrate an example of the use of the dual line protractor 10 to measure angles between body members at a joint between the body members. The view of the patient 35 is from above, showing the patient's head 30, a first body member (the left shoulder) 31, right shoulder 32, a second body member (the right arm) 33, and right wrist 34. In FIG. 3a attachment means 23 at the tip of first line 16 is attached to an anatomical landmark position on left shoulder 31. Attachment means 24 at the tip of second line 19 is attached to an anatomical landmark position on right wrist 34. Protractor 11 is placed on right shoulder 32 (joint). Protractor 11 is rotated so that first degree mark 35 is at first line 16 and is zero degrees. Right arm 33 is extended as far right as possible so that, in this case, second line 19 is at second degree mark 36 which is 200 degrees. Thus, the angle between the left shoulder 31 and the right arm 33 in this instance is 200 degrees. In FIG. 3b the right arm 33 is moved towards the left shoulder 31 as close as possible so that, in this case, second line 19 is at third degree mark 37 which is 20 degrees. Thus, the angle between the left shoulder 31 and the right arm 33 in this instance is 20 degrees. The complete range of motion of the right arm 33 at the right shoulder joint 32, relative to the left shoulder 31, is 180 degrees (200 degrees minus 20 degrees). The application of the dual line protractor 10 for these measurements is simple and rapid, requiring only a few minutes, so that the range of motion of several joints with several repeat measurements can be performed in a relatively short period of time. A major advantage of the present invention is that the tip of the line can be attached directly to a specific anatomical landmark on a body member, producing remarkable accuracy and precision in the measurement of angles between the anatomical landmarks and between the body members. Because string-like lines are used to indicate the degree marks, the dual line protractor 10 does not interfere with the natural motion of the body member being measured, allowing accurate dynamic joint angle measurement. As noted above, the movements of the lines 16 and 19 across degree marks 12, as patient 35 moves a body member, can be recorded with photographic and/or video devices, and the rate and extent of joint angle movement can be measured from these recordings by methods known in the art.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the lines can be made of any suitable material such as string, twine, plastic, and the like. The lines can have distance markings on them, such as inches or centimeters. One of the housings can be fixed to the central axis. A handle can be fixed to the protractor to facilitate holding it in place, or attachment means can be fixed to the protractor to attach it to a body member or joint. The protractor may encompass only a semi-circle. The dual line protractor can be used to measure the angles between any two points on any other objects besides body members.

It will be understood that various changes in the details, materials, and arrangements of the parts which have been described and illustrated above in order to explain the nature of this invention may be made by those skilled in the art without departing from the principle and scope of the invention as recited in the following claims.

I claim:
1. A dual line protractor, comprising:
a) a protractor fixed to a central axis, said protractor having degree marks on its circumference;
b) two spools rotatably mounted on said central axis, said spools having retractable lines; and
c) each said spool contained in a separate housing, each of said housings being rotatably mounted on said central axis so as to rotate relative to said protractor, whereby said lines are extendable from said housings across said degree marks on said protractor.

2. The dual line protractor of claim 1, further comprising each said housing having a guide to guide said line out of or into said housing as said line is extended from or retracted onto said spool, wherein each of said guides extends across said degree marks.

3. The dual line protractor of claim 2 wherein said guides are angled towards said protractor.

4. The dual line protractor of claim 1 wherein said housings and said spools rotate independently from each other on said central axis, and said retractable lines indicating angles as said retractable lines extend across said degree marks.

5. The dual line protractor of claim 1 wherein said spools are biased to retract said lines onto said spools.

6. The dual line protractor of claim 1 further comprising a base fixed to said axis, wherein said housings are positioned between said base and said protractor, and said base is parallel to said protractor.

7. A dual line protractor, comprising:
a) a protractor fixed to a central axis, said protractor having degree marks on its circumference;
b) two spools rotatably mounted on said central axis, said spools having retractable lines;
c) each said spool contained in a separate housing, each of said housings being rotatably mounted on said central axis so as to rotate relative to said protractor, whereby said lines are extendable from said housings across said degree marks on said protractor; and
d) said housings and said spools rotating independently from each other on said central axis, and said retractable lines indicating angles as said retractable lines extend across said degree marks.

8. The dual line protractor of claim 7, further comprising each said housing having a guide to guide said line out of or into said housing as said line is extended from or retracted onto said spool, wherein each of said guides extends across said degree marks.

9. The dual line protractor of claim 8 wherein said guides are angled towards said protractor.

10. The dual line protractor of claim 7 wherein said spools are biased to retract said lines onto said spools.

11. The dual line protractor of claim 7 further comprising a base fixed to said axis, wherein said housings are positioned between said base and said protractor, and said base is parallel to said protractor.

12. A dual line protractor, comprising:
a) a protractor fixed to a central axis, said protractor having degree marks on its circumference;
b) two spools rotatably mounted on said central axis, said spools having retractable lines;
c) each said spool contained in a separate housing, each of said housings being rotatably mounted on said central axis so as to rotate relative to said protractor, whereby said lines are extendable from said housings across said degree marks on said protractor;
d) said housings and said spools rotating independently from each other on said central axis, and said retractable lines indicating angles as said retractable lines extend across said degree marks;
e) each said housing having a guide to guide said line out of or into said housing as said line is extended from or retracted onto said spool, wherein each of said guides extends across said degree marks; and
f) said spools being biased to retract said lines onto said spools.

13. The dual line protractor of claim 12 wherein said guides are angled towards said protractor.

14. The dual line protractor of claim 12 further comprising a base fixed to said axis, wherein said housings are positioned between said base and said protractor, and said base is parallel to said protractor.

* * * * *